US00PP23320P2

(12) United States Plant Patent
Smith

(10) Patent No.: US PP23,320 P2
(45) Date of Patent: Jan. 8, 2013

(54) ***ASTER* PLANT NAMED 'SYAST DRAIP'**

(50) Latin Name: ***Symphyotrichum* hybrid**
Varietal Denomination: Syast Draip

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 107 days.

(21) Appl. No.: 12/932,909

(22) Filed: Mar. 9, 2011

(51) Int. Cl.
*A01H 5/00* (2006.01)

(52) U.S. Cl. ..... Plt./355
(58) Field of Classification Search ..... Plt./355
See application file for complete search history.

(56) References Cited

PUBLICATIONS

The American Gardener. Nov./Dec. 2004, pp. 46-48.*

* cited by examiner

*Primary Examiner* — June Hwu
(74) *Attorney, Agent, or Firm* — Joshua L. Price

(57) ABSTRACT

A new *Aster* plant named 'Syast Draip' particularly distinguished by the upright, rounded and freely branching growth habit, dark green foliage, with violet colored ray florets.

1 Drawing Sheet

Latin name of the genus and species of the plant claimed: *Symphyotrichum* hybrid.

Varietal denomination: 'Syast Draip'.

BACKGROUND OF THE NEW PLANT

The present invention comprises a new *Aster*, botanically know as *Symphyotrichum* hybrid, and hereinafter referred to by the variety name 'Syast Draip'.

'Syast Draip' is a product of a planned breeding program. The new cultivar 'Syast Draip' has upright, rounded and freely branching growth habit, dark green foliage, with violet colored ray florets.

'Syast Draip' originates from an open pollinated hybridization made in August 2003 in a controlled breeding program in Salinas, Calif. The female parent was 'Yodaydream', U.S. Plant Pat. No. 16,366, with lighter violet flowers, larger disc area, larger plant habit, and slower natural season flowering response. The resultant seed was sown in April 2004 in Alva, Fla.

'Syast Draip' was selected as one flowering plant within the progeny of the stated cross in the September 2004 in a controlled environment in Alva, Fla.

The first act of asexual reproduction of 'Syast Draip' was accomplished when vegetative cuttings were taken from the initial selection in October, 2004 in a controlled environment in Alva, Fla.

BRIEF SUMMARY OF INVENTION

Horticultural examination of plants grown from cuttings of the plant initiated in October 2004, and continuing thereafter, has demonstrated that the combination of characteristics as herein disclosed for 'Syast Draip' are firmly fixed and are retained through successive generations of asexual reproduction.

A Plant Breeder's Right for this cultivar has been applied for in Canada on Mar. 19, 2010 (No. 10-6888). 'Syast Draip' has not been made publicly available more than one year prior to the filing of this application.

'Syast Draip' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Aster* as a new and distinct variety.

BRIEF DESCRIPTION OF THE PHOTOGRAPHS

The accompanying photographic drawing shows typical flower and foliage characteristics of 'Syast Draip' with colors being as true as possible with an illustration of this type. The photographic drawing shows a flowering potted plant of the new variety, and a close-up of the flower.

DETAILED BOTANICAL DESCRIPTION

The plant used for the photographs was about 12 weeks old, grown in a 1 gallon pot in an outdoor trial in Gilroy, Calif.

The plant descriptions and measurements were taken in Gilroy, Calif. in May 2010 under natural light. Plants were grown under conditions which approximate those generally used for potted *Aster* trials in a greenhouse. These plants used in the descriptions were about 10 weeks old.

Color Chart used: Royal Horticultural Society Colour Chart (R.H.S.) 2001

TABLE 1

DIFFERENCES BETWEEN THE NEW VARIETY 'SYAST DRAIP' AND A SIMILAR VARIETY

| | 'Syast Draip' | 'Yodragon' (U.S. Plant Pat. No. 15,906) |
|---|---|---|
| Flower lastingness: | Lasts 20% longer | Average |
| Growth habit: | Mounded/more full | Semi-upright/less full |

TABLE 1-continued

DIFFERENCES BETWEEN THE NEW VARIETY 'SYAST DRAIP' AND A SIMILAR VARIETY

| | 'Syast Draip' | 'Yodragon' (U.S. Plant Pat. No. 15,906) |
|---|---|---|
| Flowering response under black cloth: | 33 days | 30 days |
| Flowering response in natural/fall season: | ½ week slower | Faster to flower |

Plant:
- *Form, growth and habit.*—Stems upright, freely branching, rounded habit, strong and moderately vigorous growth habit.
- *Plant height.*—18-20 cm.
- *Plant height (inflorescence included).*—22-24 cm.
- *Plant width.*—37-43 cm.

Roots:
- *Number of days to initiate roots.*—10 days at about 22 degrees C.
- *Number of days to produce a rooted cutting.*—15-18 days at 22 degrees C.
- *Type.*—Fine, fibrous, free branching.
- *Color.*—RHS N155B but whiter.

Foliage:
- *Arrangement.*—Alternate, simple.
- *Immature, leaf color, upper surface.*—Slightly lighter than RHS 147A.
- *Lower surface.*—RHS 147B.
- *Mature, leaf color, upper surface.*—RHS 147A.
- *Lower surface.*—RHS 147B.
- *Length.*—3.2-4.4 cm.
- *Width.*—0.7-1.0 cm.
- *Shape.*—Ligulate.
- *Base shape.*—Fused.
- *Apex shape.*—Acute.
- *Margin.*—Entire.
- *Texture, upper surface.*—Glabrous.
- *Lower surface.*—Glabrous.
- *Color of veins, upper surface.*—RHS 144A basally becoming indistinct.
- *Color of veins, lower surface.*—RHS 144A basally becoming indistinct.

Stem:
- *Quantity of main branches per plant.*—5-6.
- *Color of stem.*—RHS 146B; becoming more RHS 147A higher up on the plant.
- *Length of stem.*—16-20 cm.
- *Diameter.*—0.2 cm.
- *Length of internodes.*—1.0-2.5 cm.
- *Texture.*—Slightly hirsute.
- *Color of peduncle.*—Closest to RHS 147A but lighter.
- *Length of peduncle.*—2.5-3.0 cm.
- *Peduncle diameter.*—0.1-0.15 cm.
- *Texture.*—Slightly hirsute.

Inflorescence:
- *Type.*—Daisy-type, solitary inflorescences borne terminally above foliage, ray florets arranged acropetally on a capitulum.
- *Natural season flowering.*—Early September in the north.
- *Quantity of inflorescences per plant.*—80-90, plus numerous buds.
- *Lastingness of individual blooms on the plant.*—3-4 weeks.
- *Fragrance.*—None.

Bud (just when opening/showing color):
- *Color.*—Between RHS 90B and 90C.
- *Length.*—1.2-1.3 cm.
- *Width.*—0.5-0.7 cm.
- *Shape.*—Oblate.

Immature inflorescence:
- *Diameter.*—2.7-2.9 cm.
- *Color of ray florets, upper surface.*—RHS 87A with a slight white spot basally of RHS 155B.
- *Lower surface.*—Closest to RHS N88D.

Mature inflorescence:
- *Diameter.*—3.5-3.7 cm.
- *Depth.*—1.0-1.5 cm.
- *Total diameter of 'disc'.*—1.2-1.3 cm.
- *Receptacle height.*—0.5 cm.
- *Receptacle diameter.*—0.8 cm.

Ray florets:
- *Average quantity of florets.*—80-100 in numerous whorls.
- *Color of florets, upper surface.*—Between RHS N87A and N88B, sometimes with a slight RHS 90B apex.
- *Lower surface.*—Closest to RHS N88D.
- *Length.*—1.3-1.4 cm.
- *Width.*—0.3 cm.
- *Shape.*—Ligulate.
- *Apex shape.*—Acute.
- *Margin.*—Entire.
- *Texture, upper surface.*—Papillose.
- *Lower surface.*—Papillose.

Disc florets:
- *Average quantity of disc florets.*—About 75.
- *Color of florets.*—RHS 2B with RHS 155C basally.
- *Length.*—1.6-1.8 cm.
- *Width.*—0.1 cm.
- *Shape.*—Tubular, elongated.
- *Apex shape.*—Acute, 5 pointed.

Phyllaries:
- *Quantity.*—About 20-30.
- *Color, upper surface.*—RHS 147A.
- *Lower surface.*—RHS 147B.
- *Length.*—0.4 cm.
- *Width.*—0.1 cm.
- *Shape.*—Ligulate.
- *Apex shape.*—Acute.
- *Based.*—Fused.
- *Margins.*—Entire.
- *Texture, upper surface.*—Glabrous.
- *Lower surface.*—Glabrous.

Reproductive organs:
- *Gynoecium.*—Present on both florets.
- *Pistil.*—1.
- *Length.*—0.7 cm.
- *Style color.*—RHS 155C.
- *Style length.*—0.5-0.6 cm.
- *Stigma color.*—RHS 1B.
- *Stigma shape.*—Bi-parted.
- *Androecium.*—Present on disc florets only.
- *Stamens.*—1.
- *Color of filaments.*—RHS 155C.
- *Length filaments.*—0.3-0.4 cm.
- *Anther color.*—RHS 5B.
- *Anther shape.*—Oval.

*Color of pollen*.—RHS 3D.

*Pollen amount*.—Poor.

*Fertility/seed set*.—Has not been observed on this hybrid.

Disease/pest resistance: Disease/pest resistance has not been observed on this hybrid.

What is claimed is:

1. A new and distinct variety of *Aster* plant named 'Syast Draip' substantially as illustrated and described herein.

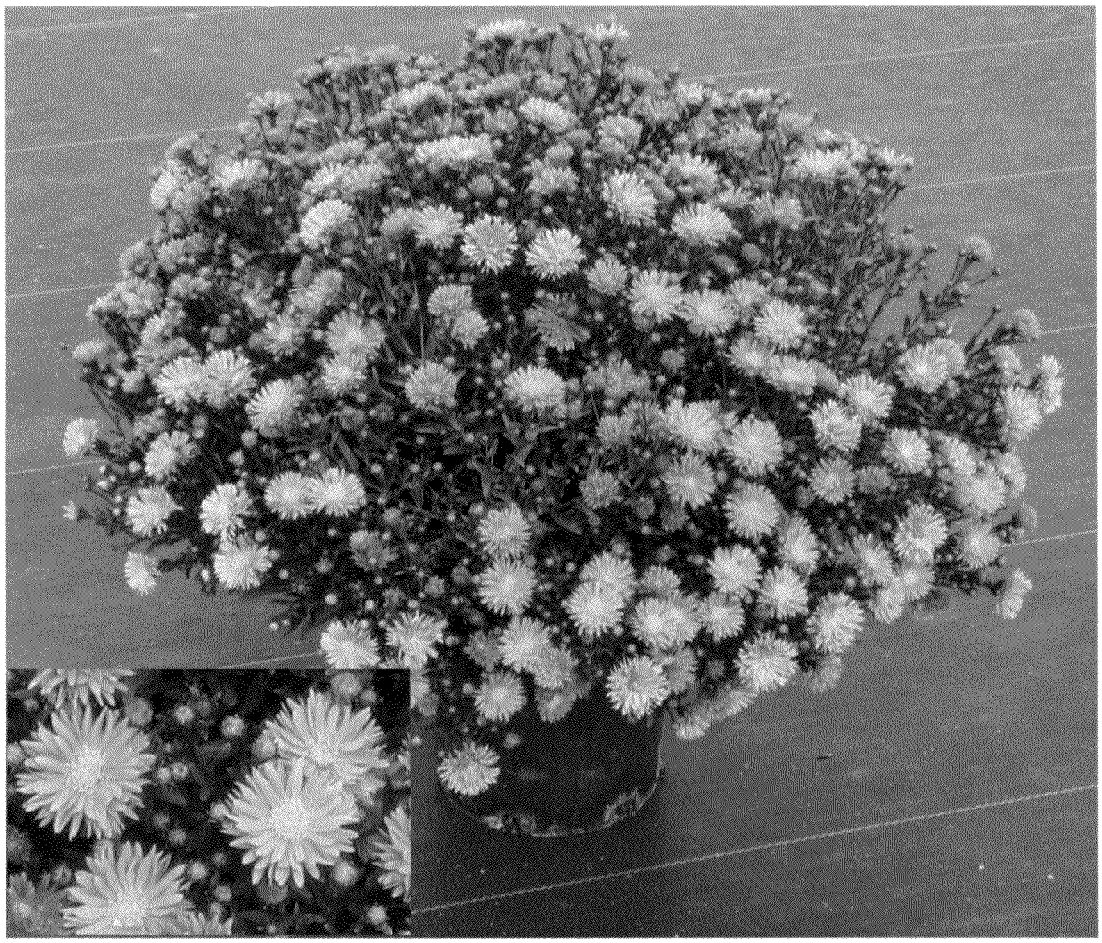

* * * * *